United States Patent [19]
Gustafson

[11] Patent Number: 6,114,653
[45] Date of Patent: Sep. 5, 2000

[54] METHOD OF CUTTING HOLLOW WORKPIECES WITH A LASER

[75] Inventor: Gary E. Gustafson, Darwin, Minn.

[73] Assignee: Spectralytics, Inc., Litchfield, Minn.

[21] Appl. No.: 09/212,465

[22] Filed: Dec. 16, 1998

Related U.S. Application Data

[62] Division of application No. 08/736,533, Oct. 24, 1996, Pat. No. 5,852,277.

[51] Int. Cl.[7] .................................................... B23K 26/08
[52] U.S. Cl. ....................................... 219/121.72; 82/1.11
[58] Field of Search ....................... 219/121.67, 121.72, 219/121.82, 121.6, 121.68, 121.69, 121.7, 121.71; 82/1.11; 83/54

[56] References Cited

U.S. PATENT DOCUMENTS

| | | | |
|---|---|---|---|
| 5,026,965 | 6/1991 | Ohe et al. ....................... | 219/121.82 X |
| 5,221,824 | 6/1993 | Saeda et al. ........................ | 219/121.82 |
| 5,267,381 | 12/1993 | Wright et al. ......................... | 82/1.11 X |
| 5,744,778 | 4/1998 | Kash et al. ......................... | 219/121.67 |

FOREIGN PATENT DOCUMENTS

| | | | |
|---|---|---|---|
| 4124546 | 1/1993 | Germany ............................ | 219/121.82 |
| 63-273584 | 11/1988 | Japan .................................. | 219/121.67 |
| 1-259830 | 10/1989 | Japan .................................. | 219/121.72 |
| 5-8065 | 1/1993 | Japan .................................. | 219/121.67 |
| 5-293681 | 11/1993 | Japan .................................. | 219/121.67 |
| 8-187595 | 7/1996 | Japan .................................. | 219/121.82 |

*Primary Examiner*—Gregory Mills
*Attorney, Agent, or Firm*—James W. Miller

[57] ABSTRACT

An improved method of cutting a pattern in a hollow, tubular workpiece to form a stent or the like involves the use of a novel workpiece fixture. The workpiece fixture is rigidly carried on a laser cutting tool to support a long piece of stock tubing in a cantilever manner beneath the laser beam of the cutting tool. The fixture is spaced from the laser beam by a distance which is in a range of approximately the same as to slightly greater than the length of any axial repeat in the pattern. The laser beam cuts the pattern in the stock tubing piece as the stock tubing is advanced past the laser beam. Accuracy is increased because the workpiece fixture is carried on the laser cutting tool, and because the cutting takes place in a zone that is close to the end of the fixture and the cantilever support provided thereby.

6 Claims, 2 Drawing Sheets

METHOD OF CUTTING HOLLOW WORKPIECES WITH A LASER

This application is a division of application Ser. No. 08/736,533, filed Oct. 24, 1996, now U.S. Pat. No. 5,852,277.

TECHNICAL FIELD

This invention relates to a method of and an apparatus for cutting hollow workpieces. More particularly, this invention is useful in manufacturing small, thin-walled, tubular devices known as stents, used in keeping coronary arteries open after an angioplasty procedure.

BACKGROUND OF THE INVENTION

Coronary angioplasty is a medical procedure used to treat blocked coronary arteries as an alternative to a coronary bypass operation. It involves the insertion of a balloon catheter into the blocked artery and the inflation of the balloon to expand the size of the artery and relieve the blockage. While the procedure is often effective in opening the artery, one problem is the tendency of the artery to reclose. This requires that the angioplasty procedure be repeated which is obviously expensive and may be risky for the patient.

In recent years, small cylindrical tubes called stents have been inserted into the artery after a coronary angioplasty procedure. The stents are made of a thin-walled metallic material and have a pattern of apertures or holes cut around the circumference of the stent along most of its length. The purpose of the stent is to reinforce the walls of the artery after an angioplasty to prevent reclosing of the artery or to at least prolong the time the artery takes to reclose. The pattern in a stent is typically cut by a laser cutting tool.

In manufacturing stents, basic lathe techniques have been adapted to support the tubing used to form the stent during the hole cutting process. Typically, a piece of tubing is supported between a drive mechanism and a tail stock support in the manner of a lathe. A laser cutting tool positioned above the tubing will cut the pattern by moving relative to the tubing along the length of the finished stent, the tubing being rotated as necessary to present different parts of the circumference to the laser cutting tool. After the pattern is completely cut in the stent, the tubing is cut first at the tail stock end and then at the drive end of the stent to allow a finished stent to be completed.

This manufacturing method has various limitations which results in a fairly high scrap rate. For example, because the pattern typically occupies a large percentage of the surface area of the stent, the stent may sag or bow downwardly during the cutting process as the pattern is cut and the cut area becomes larger. This is particularly true for thin walled material of the type most desirably used to form stents. In addition, friction from the tail stock mechanism often cause manufacturing errors throughout the part. Accordingly, many stents are rejected as failing to meet the necessary cut accuracy when manufactured by the methods used prior to this invention.

Another difficulty is alignment of the drive mechanism and tail stock support with the laser cutting tool. These items are not directly coupled to one another. Accordingly, if any of the drive mechanism, tail stock support, or laser cutting tool are bumped or jarred during the manufacturing operation, further errors will occur. This is a further contributing factor to the relatively high scrap rate of these devices.

SUMMARY OF THE INVENTION

This invention relates to a method of and apparatus for cutting a pattern along the length of a thin walled, hollow workpiece, such as a stent, which is much more reliable and has much less scrap than known methods.

The method of this invention comprises supporting the workpiece at one end in a cantilever manner by a support fixture. The cutting tool is positioned past the end of the support fixture by a distance which is much less than the desired length of a finished workpiece. A first end of the stent is cut when that end first passes beneath the cutting tool and then the pattern is progressively cut as the tubing is advanced beneath the cutting tool, with the tubing being rotated as needed beneath the cutting tool to cut the pattern around the circumference of the tubing. However, because the distance between the cutting tool and the point of support for the tubing is relatively short in comparison to the length of the finished workpiece, the tubing does not sag or bow downwardly in this short distance, yielding improved accuracy and yield in the manufacturing method of this invention.

The apparatus of this invention comprises a workpiece fixture for holding the tubing beneath the laser cutting tool and for supporting the tubing in a cantilever fashion. The workpiece fixture is rigidly affixed to the laser cutting tool. Thus, bumping either the cutting tool or the fixture does not disturb the accuracy of the cut part as the two move together, again increasing the accuracy and yield of the manufacturing method of this invention.

BRIEF DESCRIPTION OF THE DRAWINGS

This invention will be described more completely hereafter in the Detailed Description, when taken in conjunction with the following drawings, in which like reference numerals refer to like elements throughout.

DETAILED DESCRIPTION

Figure 1:
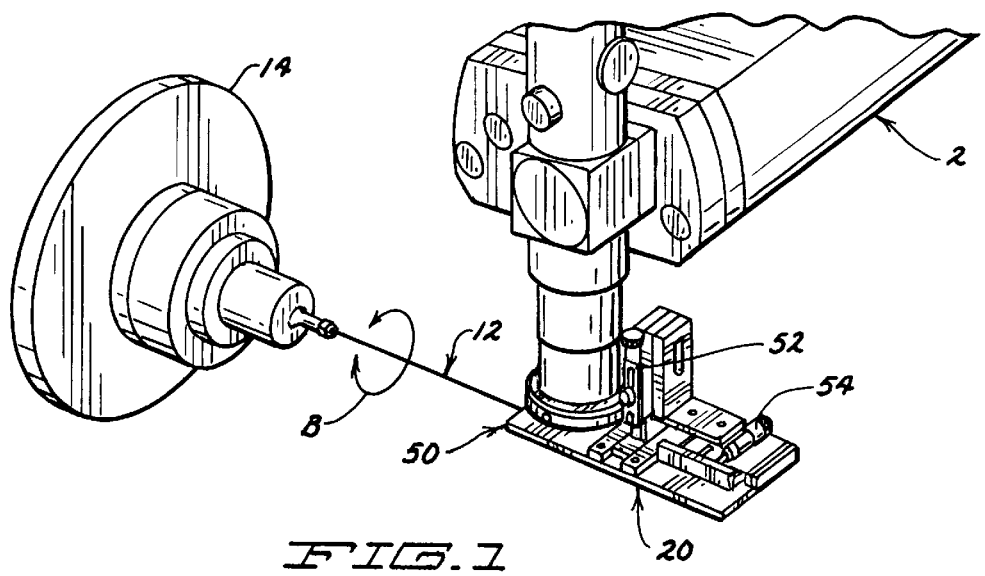
FIG. 1 is a perspective view of the apparatus of this invention used to conduct the method of this invention, particularly illustrating a laser cutting tool with the workpiece fixture attached to the cutting tool for receiving a long piece of stock tubing.
Figure 2:
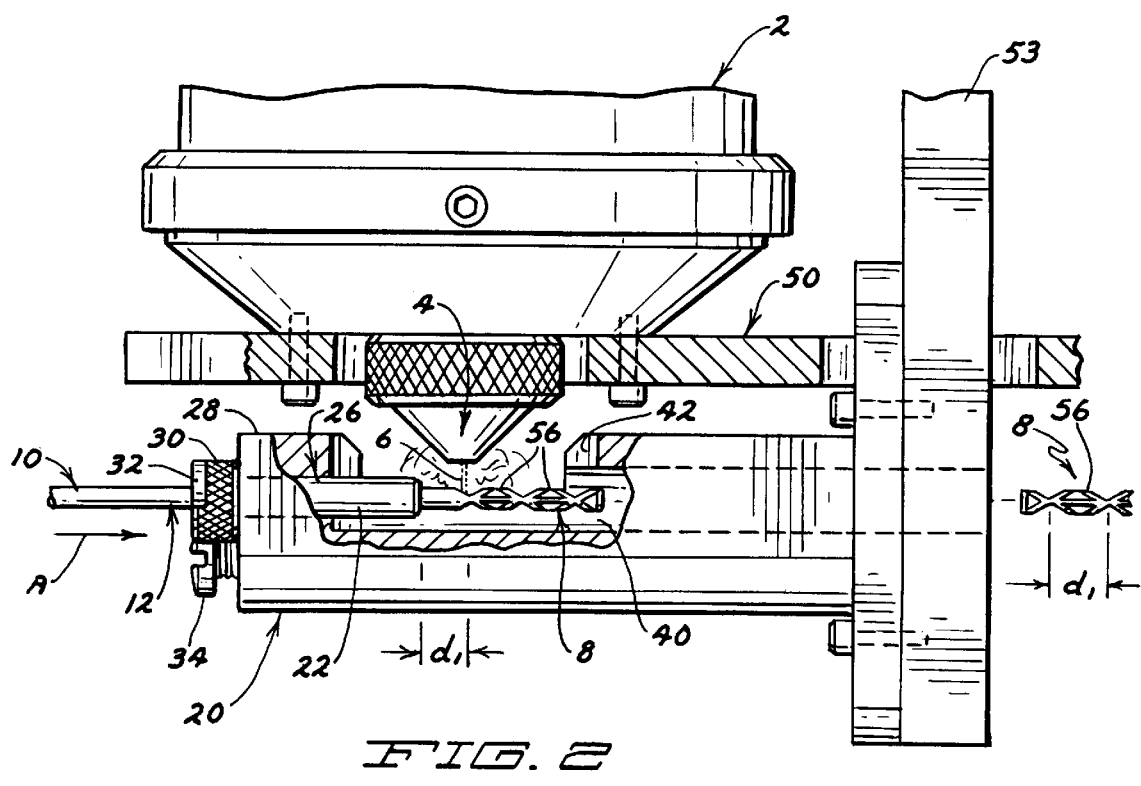
FIG. 2 is a partial side elevational view of the apparatus of this invention, particularly illustrating the laser cutting tool and conjoined workpiece fixture and illustrating the apparatus being used to cut hollow workpieces of predetermined length from a long piece of stock tubing.
Figure 3:
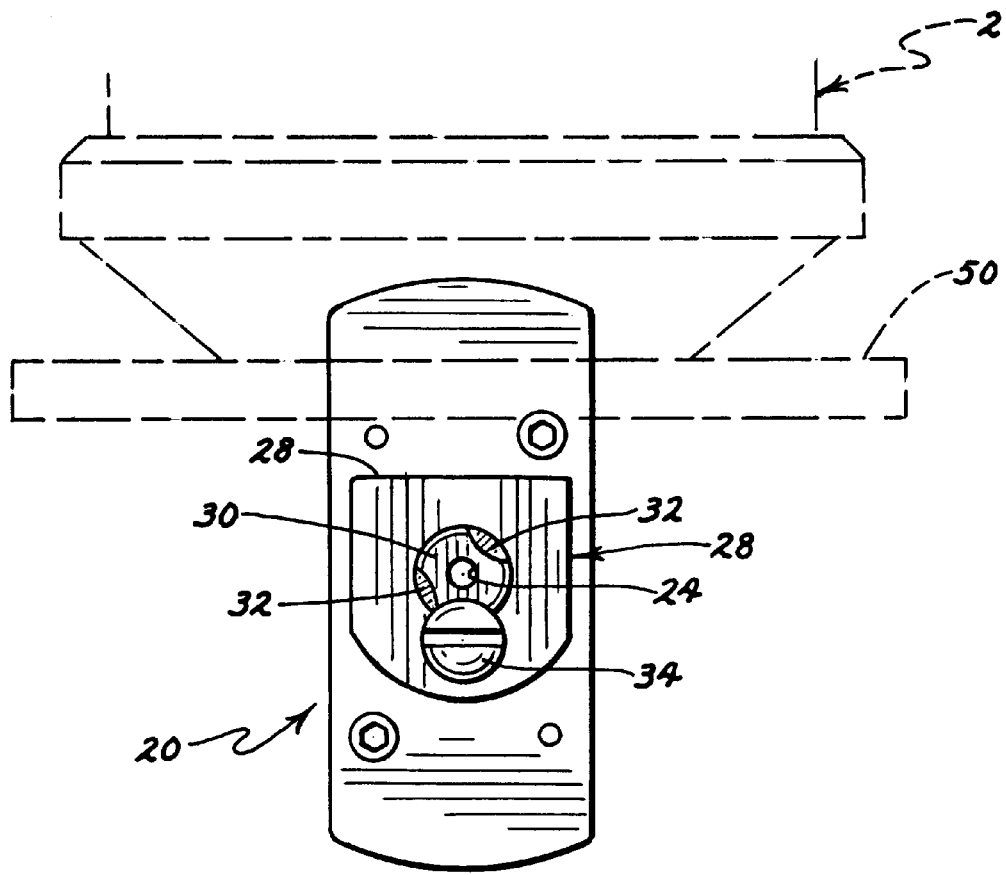
FIG. 3 is a front elevational view of the workpiece fixture of this invention.

Referring first to FIGS. 1 and 2, a laser cutting tool is illustrated generally as 2 having a nozzle 4. Laser cutting tool 2 generates a downwardly directed laser beam 6. Laser beam 6 cuts apertures or holes around the circumference and along the length of a hollow workpiece 8. A finished workpiece 8 will have a predetermined length which can be varied as desired.

Workpieces 8 produced by this invention preferably comprise, but are not limited to, medical devices known as stents. This invention is capable of producing stents of longer length with greater accuracy and less scrap than prior art manufacturing methods.

The hollow tubing 10 from which workpieces 8 are cut may be provided in very long pieces, much longer than the length of finished workpieces 8, so that multiple finished workpieces 8 can be cut from one piece of stock tubing. One long piece of stock tubing is shown as 12 in FIG. 1. A conventional drive mechanism 14 is provided for axially advancing the stock tubing piece 12 beneath laser cutting tool 2 as indicated by the arrow A in FIG. 2. Similarly, drive mechanism 14 is also capable of rotating stock tubing piece 12 about its axis as indicated by the arrow B in FIG. 1. One particular type of drive mechanism 14 known in the art is an indexable rotary drive of various types manufactured by Aerotech or others.

The apparatus of this invention comprises a workpiece fixture 20 for supporting stock tubing piece 12 in a cantilever manner beneath cutting tool 2. Workpiece fixture 20 includes a cylindrical bushing 22 having a central bore 24 extending all the way through bushing 22. Bushing 22 is itself removably inserted into a cylindrical passage 26 in a fixture body 28. Thus, bushing 22 extends a short distance into one end of fixture body 28 with bushing 22 having an inner end 29 located inside fixture body 28.

Bushing 22 has an enlarged head 30 that is positioned immediately outside of fixture body 28 when bushing 22 is inserted into fixture body 28. Bushing head 30 has arcuate recesses or grooves 32 that cooperate with the head of a screw 34 for locking or holding bushing 22 in place. This allows bushing 22 to be easily removed and replaced with other bushings 22 having different inner diameters for bore 24 to accommodate different outer diameters of stock tubing piece 12. Thus, screw 34 can be removed to disengage one bushing 22, that bushing 22 can be pulled out of the end of fixture body 28 by pulling outwardly on bushing head 30, a new and/or different bushing 22 can be inserted into fixture body 28, and the screw 34 can be reinstalled to lock the new and/or different bushing 22 in place.

Fixture body 28 includes a longitudinal channel 40 that extends from the location of bushing 22 through the remaining length of fixture body 28. Channel 40 is considerably larger than the outside diameter of stock tubing piece 12 and indeed even somewhat larger than the outside diameter of bushing 22. Channel 40 defines an exit passage for finished workpieces 8 after workpieces 8 have been cut. Bushing 22 is aligned with channel 40 so that stock tubing piece 12 can pass on into channel 40 after passing through bore 24 of bushing 22. Channel 40 opens through the other end of fixture body 28 to allow finished workpieces 8 to exit out through channel 40.

Figure 4:
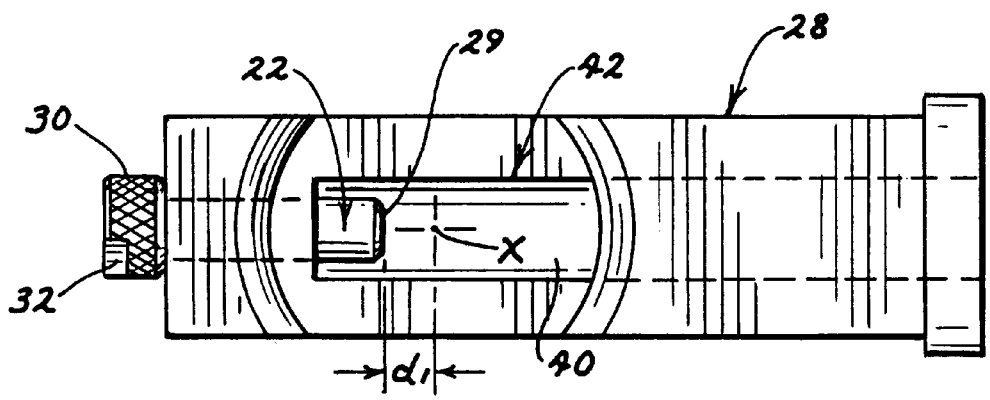
FIG. 4 is a top plan view of the workpiece fixture of this invention.

The top of fixture body 28 has an aperture 42 to allow laser beam 6 to pass downwardly into fixture body 28 proximate to, but spaced from, inner end 29 of bushing 22. Referring to FIG. 4, the aperture is sufficiently large to expose the inner end of longitudinal channel 40 and inner end 29 of bushing 22. The focal point of laser beam 6 is indicated as x in FIG. 4. This focal point x is spaced from inner end 29 of bushing 22 by a relatively short distance indicated as $d_1$ in FIG. 4.

Fixture body 28 is rigidly mounted or fixed to laser cutting tool 2 by a support structure generally indicated as 50. Support structure 50 includes a vertical adjuster 52 and a horizontal adjuster 54 so that the distance $d_1$ can be adjusted and so that the axis of bore 24 of bushing 22 can be aligned with the focal point x of laser beam 6. Any suitable support structure 50 and any suitable vertical and horizontal adjusters 52 and 54 for moving bushing 22 vertically and horizontally could be used. For example, fixture body 28 could be attached to a vertical plate which can be moved vertically by vertical adjuster 52 and which can be moved horizontally by horizontal adjuster 54. However, once particular vertical and horizontal adjustments have been made during machine setup, fixture body 28 thereafter is directly carried on laser cutting tool 2 in a fixed, spatial relationship. Thus, inadvertent movement of either fixture body 28 and/or laser cutting tool 2 will carry the other component with it to maintain the desired relationship of the focal point x of laser beam 6 relative to inner end 29 of bushing 22.

With respect to the use of this apparatus in the practice of the method of this invention, a relatively long stock tubing piece 12 is inserted through bore 24 of bushing 22 until it passes out into channel 40. During the setup of fixture 20, focal point x of laser beam 6 is spaced a relatively short distance $d_1$ away from inner end 29 of bushing 22. Preferably, distance $d_1$ is in a range of approximately the same as to slightly greater than the length of any axial repeats 56 in the pattern being cut in workpiece 8. Thus, if a pattern is being cut having axial repeats 56 having a length l1 as shown in FIG. 2, then laser beam 6 is spaced away from inner end 29 of bushing 22 by a distance $d_1$ which is in the range of from approximately the same as to slightly greater than the length l1 of repeat 56.

It is apparent that stock tubing piece 12 is supported in bushing 22 in a cantilever manner at one end only as the inner diameter of bore 24 is slightly greater than the outer diameter of stock tubing piece 12. To begin forming finished workpieces 8, stock tubing piece 12 is advanced through workpiece 8 beneath laser cutting tool 2. At some starting point, the front end of workpiece 8 is cut by severing stock tubing piece 12 from that having gone before. Cutting tool 2 then begins cutting the pattern with drive mechanism 14 advancing or retracting stock tubing piece 12 beneath laser cutting tool 2 and rotating tubing piece tool 2 as needed to cut the desired pattern.

Because the distance $d_1$ is preferably approximately the same as to slightly greater than the length l1 of any axial repeat 56 in the pattern, there is never any need to draw any portion of the cut back into bore 24 of bushing 22. The entire repeat 56 can be cut around the entire circumference of stock tubing piece 12 with drive mechanism 14 moving stock tubing piece 12 back and forth beneath laser cutting tool 2 but without ever drawing any portion of the cut back into bushing 22. Thus, there is no possibility that any burrs or edges of the cut will catch or scrape against inner end 29 of bushing 22.

However, the foregoing $d_1/l_1$ relationship is strictly necessary only when roughness is generated at the cut edge. This roughness would potentially create friction in bushing 22, and thus possibly introduce manufacturing errors, if the cut edge were to be drawn back into the bushing. If a smooth edge can be cut into the particular material comprising the workpiece during cutting of the pattern, then drawing the cut edge back into bushing 22 would not be harmful. In this case, the distance $d_1$ could be less than the distance $l_1$.

After a first portion of the pattern is cut, i.e. after a first axial repeat 56 is cut, drive mechanism 14 again advances stock tubing piece 12 further beneath laser cutting tool 2 to begin cutting the next and subsequent repeats 56. Again, each repeat 56 can be cut without ever having to draw any portion of what has been cut back into bore 24 of bushing 22. Thus, each repeat 56 is cut and then stock tubing piece 12 is advanced further to begin cutting the next repeat 56. Finally, after a desired length of tubing piece 12 has been cut, equal to a desired full or partial number or repeats 56, stock tubing piece 12 can be severed by laser beam 6 at the rear end to finish workpiece 8. This finished workpiece 8 can then be pulled out through channel 40 of fixture body 28 and removed.

The cut used to form the rear end of one finished workpiece 8 may also simultaneously form the cut at the front end of the next workpiece 8. Or, a new cut could be used further down the tubing to begin the next workpiece 8 after a first workpiece is formed. In any event, the next workpiece 8 can now be cut in the same manner as the first workpiece 8. Thus, a number of finished workpieces 8 can be cut, one after another, from a single piece 12 of stock tubing.

The great advantage of the method and apparatus of this invention is the use of a cantilever support for stock tubing piece 12 and the fact that such a short unsupported distance $d_1$ exists between the inner end 29 of bushing 22 and focal point x of laser beam 6. Workpiece 8 will not sag or deform over this short distance providing greatly increased cutting accuracy. Thus, relatively long workpieces 8 can be cut with a pattern having many repeats 56 with a relatively low scrap rate. This is a tremendous advantage over prior art methods of manufacturing such workpieces, typically in the manufacturing of stents used in coronary arteries following coronary angioplasty purposes.

Stents manufactured using the method and apparatus of this invention have had a finished overall length of from approximately 15 to 55 mm with an outer diameter of approximately 1.3 mm. When manufacturing such stents, the axial repeats 56 may repeat every 3 or 4 mm, such that $d_1$ would preferably be set to approximately the same as or slightly longer than 3 or 4 mm. A maximum value for $d_1$ would be approximately 10 mm or so given the types of tubing commonly used to form stents of this diameter, these values can obviously change according to different tubing sizes or repeat lengths. In any event, an important aspect of this invention is to keep $d_1$ as short as possible to prevent manufacturing errors.

The rigid attachment of workpiece fixture 20 to laser cutting tool 2 is also advantageous. It preserves the alignment accuracy even if laser cutting tool 2 is jarred or bumped as fixture 20 moves with cutting tool 2. This further simplifies setup and manufacturing accuracy. Various modifications of this invention will be apparent to those skilled in the art. Thus, the scope of the invention is to be limited only by the appended claims.

I claim:

1. A method of manufacturing a hollow, generally tubular workpiece having a pattern cut around the circumference and along the length thereof, which comprises:

(a) supporting a relatively long piece of stock tubing used to form the workpiece in a cantilever manner using a fixture, wherein a pattern is to be cut into the stock tubing while the stock tubing is supported by the fixture with the pattern having an axial repeat with at least four repeats;

(b) continuously positioning a cutting tool while the cutting tool is active past one end of the fixture by a distance which is in the range of approximately the same as to slightly greater than the length of one repeat; and (c) maintaining the fixture and the cutting tool fixed relative to one another while the cutting tool is active and while longitudinally and rotationally advancing the stock tubing piece through the fixture and past the cutting tool while the cutting tool is active to cut the pattern around the circumference and along the length of the workpiece without drawing any portion of the cut back into the fixture.

2. The method of claim 1, wherein the cutting tool comprises a laser cutting tool.

3. The method of claim 2, further including rigidly affixing the fixture to the laser cutting tool.

4. The method of claim 1, comprising the steps of:

(a) cutting a front end of the workpiece by severing through the tubing before a substantial portion of the pattern is cut; and (b) cutting a rear end of the workpiece to provide a finished workpiece after the pattern is cut.

5. The method of claim 1, wherein the pattern comprises a pattern of apertures cut along the length and around the circumference of the workpiece.

6. The method of claim 1, wherein the workpiece forms a stent.

* * * * *